Jan. 27, 1942. F. H. HOWARD Plant Pat. 501
ROSE PLANT
Filed Aug. 19, 1941
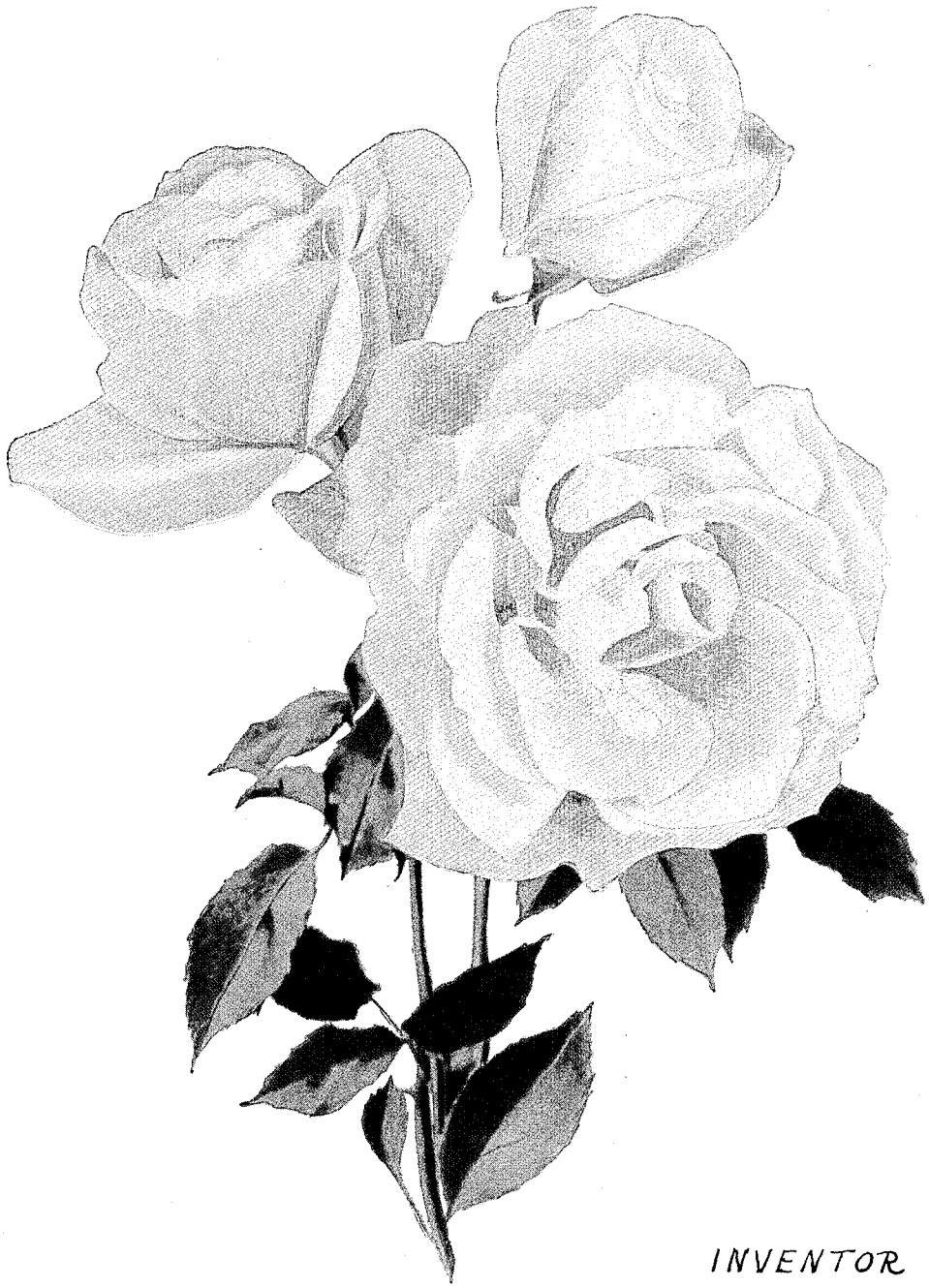
INVENTOR
Frederick Huber Howard
By Orville M. Kile
Plant Pat. Agt.

Patented Jan. 27, 1942

Plant Pat. 501

UNITED STATES PATENT OFFICE

501

ROSE PLANT

Frederick Huber Howard, Montebello, Calif.

Application August 19, 1941, Serial No. 407,482

1 Claim. (Cl. 47—61)

My invention relates particularly to a new variety of red hybrid tea rose plant which resulted from a controlled cross between Crimson Glory and an unnamed seedling, the cross having been made by me at my nurseries in Montebello.

The outstanding quality of this rose variety is attested by the fact that it was the all America rose selection for 1941. The committee making this selection predicted that this new rose would replace all existing red roses as the leader of its type. It is valuable both as a garden rose and as a greenhouse forcing rose.

I have asexually reproduced this new variety for several years and the large stock that I have accumulated retains the characteristics of the original, thus showing that these characteristics have become firmly fixed.

There is no other red rose with which this new variety can adequately be compared. It has a number of the qualities of its present, Crimson Glory, but differs radically in many respects. The blooms are of course entirely different in color although both are "red."

The original illustrations which are a part of this application represent the spring blooms of this new variety and show an opening bud, a bloom approximately three-fourths open, and a bloom which has been open several days; together with some of the stems and foliage. In the original these are shown in approximately natural size and as true to color as the artist could depict them.

A detailed description of the plant and flower follows. Color plate references indicate Ridgway's Color Standards and Nomenclature, but where no plate number is given the ordinary dictionary term is intended.

*The plant*

Growth: Very vigorous upright bush, attaining a height of 3½ to 4 feet. Hardy in temperate climates.

Blooming habit: Free and continuous bloomer, persistent in the production of large blossoms from spring to winter frost.

Stem: Long, exceedingly stout; internodes short and inclined to be somewhat staggered.

*Color.*—Cerro Green (Plate V).

*Thorns.*—Medium in size; many; irregularly spaced; sharp; downward pointing; greenish white to light brown.

Foliage: Healthy, because very disease resistant; abundant.

*Leaves.*—Compound, with three to seven leaflets.

*Leaflets.*—*Shape*—ovate with accuminate apex; edges finely and sharply serrated. *Size*—small to medium; terminal leaflet varies from 2 to 2¾ inches in length and 1¼ to 1⅜ inches in width. Lateral leaflets are much smaller. *Color*—between Elm Green and Forest Green (Plate XVII) on the upper surface, and approximately Light Hellebore Green (Plate XVII) on the surface.

*Rachis.*—Red-tinged and grooved above; below smooth and same color as under surface of leaves.

*Stipules.*—Medium in length and width. Clinging, except for the long, non-curling points.

*Peduncle.*—Sturdy; smooth except for one or two thorns; Oil Green (Plate V), lightly tinged with reddish brown; short, averaging 2 to 2½ inches, thus bringing foliage close to flower.

*The Flower*

Bud:

*Size.*—Large. When calyx breaks it is about ¾ inch long and ½ to ⅝ inch wide at base. Before expanding into a flower it is 2 to 2½ inches long.

*Shape.*—When calyx breaks it is short and very broad at the base, terminating in a very sharp point. As it develops it becomes relatively longer and is approximately 2 inches long just before unfolding. The bud is exceptionally long and well developed at this stage, being pointed and somewhat inclined to be urn-shaped as it opens.

*Color.*—Approximately Carmine (Plate I) as the calyx breaks. Lightens as it opens and becomes the clear beautiful shade of crimson which is found in the blossom.

*Opening.*—Slow and even.

Bloom:

*Size.*—Large, approximately 4½ inches in diameter as an average.

*Form.*—The blooms of the cool spring weather differ from those of the hot weather in shape as well as in color tone. The early spring blooms are high-centered, opening finally into cup-shape. The half-opened bloom is particularly beautiful in its form, the inner petals retaining the high center while the outer petals spread. Because of the form and the heavy substance of the petals the flower appears very large and full even though it has relatively few petals.

The hot weather blooms are much more globular in shape—in fact almost "cabbage-shaped," with very deep-cupped petals. The inner petals of the half-open flower retain the globular shape while the outer petals spread only slightly, all of the petals curling back slightly at the edges. Some of these summer blooms open into cup shape but the greater number retain the globular shape until late in their development or until they die. This gives the effect of a very heavy rose, although it has relatively few petals.

*Petalage.*—Double, having 25 to 30 petals.

*Petals.*—*Size*—outer petals 2 by 2¼ inches. *Shape*—almost circular, usually with slight notch at top. The summer blooms have petals that are very deep-cupped; the spring blooms have petals only slightly cupped but which reflex slightly when opening. *Substance*—heavy, somewhat like the petals of Red Radiance. *Color*—the colors of the spring blooms and the summer blooms differ somewhat but neither is found in Ridgway's Color Standards and Nomenclature. The spring blooms are a beautiful shade of bright crimson without any traces of scarlet or maroon. The nearest we can describe the color by use of Ridgway's is to say that it lies between Rose Red (Plate XII) and Carmine (Plate I), but that is a wide range and does not give an adequate description of the color. It is much more brilliant than Rose Red and also somewhat deeper, yet it does not fall in the color range of Plate I.

The summer blooms lean slightly more toward Tyrian Rose (Plate XII) and there is greater contrast between the upper and under surfaces, the latter being slightly lighter and of a silky appearance, while the upper surface of the outer petals is somewhat velvety in appearance. This contrast is very evident because the inner petals retain their globular form while the outer petals are somewhat spread.

*Longevity.*—The flowers are exceptionally long-lasting, especially as cut flowers.

*Fragrance.*—Intense and very lasting.

Reproductive organs:

*Pistils.*—Many; closely bunched. *Styles*—short; uneven; large portion inclosed in calyx; portion protruding from calyx is reddish tinged. *Stigmas*—light yellow.

*Stamens.*—Many, surrounding bunched pistils. *Filaments*—irregular lengths, rising above pistils in most instances. *Anthers*—large; dark yellow, approximately Primuline Yellow (Plate XVI).

Having thus disclosed my invention, I claim:

The new and distinct variety of hybrid tea rose plant herein shown and described, characterized particularly by its strong and vigorous growth; the freedom with which it produces beautiful blooms continuously from spring until frost; its large, long-pointed buds; the intense fragrance, pleasing form, excellent lasting quality, and distinctive brilliant crimson color of its large blossoms.

FREDERICK HUBER HOWARD.